United States Patent [19]

Kinney et al.

[11] Patent Number: 5,240,946
[45] Date of Patent: Aug. 31, 1993

[54] ((2-(AMINO-3,4-DIOXO-1-CYCLOBUTEN-1-YL)AMINO)ALKYL)-ACID DERIVATIVES

[75] Inventors: William A. Kinney, Churchville, Pa.; Deanna C. Garrison, Durham, N.C.

[73] Assignee: American Home Products Corporation, New York, N.Y.

[21] Appl. No.: 875,925

[22] Filed: Apr. 29, 1992

Related U.S. Application Data

[60] Division of Ser. No. 806,861, Dec. 17, 1991, Pat. No. 5,168,103, which is a continuation-in-part of Ser. No. 644,157, Jan. 22, 1991, abandoned.

[51] Int. Cl.$^5$ .................. A61K 31/41; A61K 31/215; A61K 31/19; C07C 61/04
[52] U.S. Cl. .................... 514/364; 514/381; 514/529; 514/557; 562/505; 562/11; 562/16; 560/156; 558/166; 548/132; 548/254
[58] Field of Search ............ 562/505, 11, 16; 558/166; 560/156; 548/132, 254; 514/557, 529, 364, 381

[56] References Cited

U.S. PATENT DOCUMENTS 4,390,701 6/1983 Algieri et al. .................. 546/235

OTHER PUBLICATIONS

Johnson, R. L. et al., J. Med. Chem. 1988, 31, 2057.
Choi, D. W., Trends Neurosci. 1988, 11, 465.
Boast, C. A. et al., Brain Research, 1988, 442, 345.
Lehmann, J. et al., J. Pharmacol. Exp. Ther., 1987, 240, 737.
Engelsen, B., Acta. Neurol. Scand. 1986, 74, 337.
Maragos, W. F., et al., Trends Neurosci. 1987, 10, 65.
Watkins, J. C., et al., Annu. Rev. Pharmacol. Toxicol., 1981, 21, 165.
Lehmann, J. et al., J. Pharmacol. Exp. Ther. 1988, 246, 65.
Schmutz, M. et al., Abs. Soc. Neurosci., 1988, 14, 864.
Chenard, B. L., et al., J. Med. Chem. 1990, 33, 1077.
C. A. 114 717 (1991) 246836q Tietz et al.

Primary Examiner—Mary C. Lee
Assistant Examiner—Joseph K. McKane
Attorney, Agent, or Firm—Richard K. Jackson

[57] ABSTRACT

A compound of the formula:

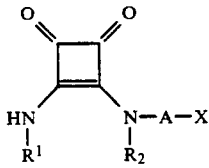

in which $R^1$ is hydrogen, alkyl or phenylalkyl; $R^2$ is hydrogen, alkyl, alkenyl or phenylalkyl; or $R^1$ and $R^2$ taken together are $-CH_2CH_2-$, $-CH_2C(R^6)(R^7)CH_2-$ or $-CH_2C(R^8)(R^9)-C(R^{10})(R^{11})CH_2-$, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms; A is alkylene or alkenylene; X is $CO_2R^3$ in which $R^3$ is hydrogen or alkyl, $P(O)(OR^4)(OR^5)$ in which $R^4$ and $R^5$ are, independently, hydrogen or alkyl, 3,5-dioxo-1,2,4-oxadiazolidin-2-yl or 5-tetrazolyl; or a pharmaceutically acceptable salt thereof are useful as neuroprotectants.

15 Claims, No Drawings

((2-(AMINO-3,4-DIOXO-1-CYCLOBUTEN-1-YL)AMINO)ALKYL)-ACID DERIVATIVES

This is a division of application Ser. No. 07/806,861 filed Dec. 17, 1991, now U.S. Pat. No. 5,168,103 granted Dec. 1, 1992, which is a continuation-in-part of U.S. patent application Ser. No. 07/644,157, filed Jan. 22, 1991, now abandoned.

BACKGROUND OF THE INVENTION

Excitatory amino acids such as glutamic acid have been shown to be important neurotransmitters (Johnson, R. L.; Koerner, J. F., *J. Med. Chem.* 1988, 31, 2057), which in excess participate in the sequence of events leading to neuronal damage after cerebral ischemia (Choi, D. W., *Trends Neurosci.* 1988, 11, 465). One important subtype of excitatory amino acid receptor is the NMDA-receptor, which is defined by the selective agonist N-methyl-D-aspartic acid (NMDA). Blocking the action of endogenous agonist by the selective NMDA-receptor antagonist 4-(3-phosphonopropyl)-2-piperazinecarboxylic acid (CPP) has been shown to prevent ischemic brain damage in gerbils (Boast, C. A. et al., *Brain Research,* 1988, 442, 345). Also, NMDA-induced convulsions have been prevented by CPP in mice (Lehmann, J. et al., *J. Pharmacol. Exp. Ther.* 1987, 240, 737). Finally, competitive NMDA antagonists such as CPP have been shown to prevent the Parkinsonian-like symptoms induced by MPTP (1-methyl-4-phenyl-1,2,3,6-tetrahydropyridine) in rats (Turski, L. et al., *Nature* 1991, 349, 414). For these reasons, NMDA-receptor antagonists are considered appropriate for treatment of epilepsy, stroke (Engelsen, B., *Acta. Neurol Scand.* 1986, 74, 337), and neurodegenerative disorders such as Alzheimer's disease (Maragos, W. F. et al., *Trends Neurosci.* 1987, 10, 65) and Parkinson's disease.

Chemical entities known to be competitive NMDA-receptor antagonists contain the α-amino-carboxylic acid and phosphonic acid functionalities separated by a variety of spacer units. An unembellished example is 2-amino-5-phosphonovaleric acid (AP5) (Watkins, J. C.; Evans, R. H., *Annu. Rev. Pharmacol. Toxicol.* 1981, 21, 165), which contains a saturated carbon chain. More complex examples, which contain elements enhancing structural rigidity and therefore potency, include CPP (see above), cis-4-(phosphonomethyl)-2-piperidinecarboxylic acid (CGS-19755) (Lehman, J. et al., *J. Pharmacol. Exp. Ther.* 1988, 246, 65), and (E)-2-amino-4-methyl-5-phosphono-3-pentenoic acid (CGP-37849) (Schmutz, M. et al., *Abs. Soc. Neurosci.* 1988, 14, 864). Although there has been effort to find groups which are bioisosteric with the phosphonic acid group (Chenard, B. L. et al., *J. Med Chem.* 1990, 33, 1077), no examples of NMDS-receptor antagonists have appeared in the literature which demonstrate a bioisosteric replacement of the α-aminocarboxylic acid functionality.

DESCRIPTION OF THE INVENTION

In accordance with this invention, there is provided a group of N-substituted 3,4-diamino-3-cyclobutene-1,2-dione derivatives which are NMDA antagonists which are recognized by the correct receptors and which prevent NMDA-induced lethality in vivo. Useful as anticonvulsants and neuroprotectants in situations involving excessive release of excitatory amino acids, the compounds of this invention present the following structural formula (I):

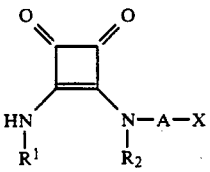

in which $R^1$ is hydrogen, alkyl of 1 to 6 carbon atoms;

$R^2$ is hydrogen, alkyl of 1 to 6 carbon atoms or phenylalkyl of 7 to 12 carbon atoms; or $R^1$ and $R^2$ taken together are Z, which is —CH$_2$CH$_2$—, —CH$_2$C(R$^6$)(R$^7$)CH$_2$— or —CH$_2$C(R$^8$)(R$^9$)—C(R$^{10}$)(R$^{11}$)CH$_2$—, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms;

A is alkylene of 1 to 6 carbon atoms or alkenylene of 2 to 6 carbon atoms;

X is CO$_2$R$^3$ in which $R^3$ is hydrogen or alkyl of 1 to 6 carbon atoms, P(O)(OR$^4$)(OR$^5$) in which $R^4$ and $R^5$ are, independently, hydrogen or alkyl of 1 to 6 carbon atoms, 3,5-dioxo-1,2,4-oxadiazolidin-2-yl or 5-tetrazolyl;

or a pharmaceutically acceptable salt thereof.

Examples of alkyl for $R^{1-5}$ and $R^{6-16}$, infra, are straight or branched groups such as methyl, ethyl, n-propyl, isopropyl, butyl and hexyl. Preferred alkyl groups have 1 to 4 carbon atoms. Examples of alkenyl for $R^2$ are straight or branched groups such as vinyl, prop-1-enyl, alkyl, methallyl, but-1-enyl, but-2-enyl and but-3-enyl.

Examples of phenylalkyl groups for $R^1$ and $R^2$ are such groups wherein the alkyl moiety is a straight or branched chain such as benzyl, phenethyl, 3-phenylpropyl, 4-phenyl butyl. Preferably the alkyl moiety of such a group contains 1 to 4 carbon atoms.

Preferred values for $R^1$ and $R^2$ are, independently, hydrogen, methyl, allyl, methallyl and benzyl, and when $R^1$ and $R^2$ are taken together as Z, they are —CH$_2$CH$_2$—, —CH$_2$C(R$^6$)(R$^7$)CH$_2$— or —CH$_2$C(R$^8$)(R$^9$)—C(R$^{10}$)(R$^{11}$)CH$_2$—, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms. Examples of alkylene groups for A are straight or branched chain groups preferably those having 1 to 4 carbon atoms such as: —CH$_2$—, —CH$_2$CH$_2$—, —CH(CH$_3$)—CH$_2$, —CH$_2$CH(CH$_3$)—, —(CH$_2$)$_3$— and —(CH$_2$)$_4$—. Examples of alkenylene groups for A are cis and trans groups preferably having 2 to 4 carbon atoms such as —CH$_2$—CH=CH—, —CH=C(CH$_3$)—, —C(CH$_3$)=CH, —CH=CH—CH$_2$— and —CH$_2$—CH=CH—CH$_2$— and —CH$_2$—CH=C(CH$_3$)—. Preferably A is alkylene of 1 to 4 carbon atoms or trans-2-butylene. Preferred values for X are carboxyl, phosphonyl or 5-tetrazolyl.

The pharmaceutically acceptable salts of the compounds of this invention include the alkali metal (sodium, potassium or lithium), alkaline earth metal (calcium or magnesium) and ammonium salts.

This invention also provides processes for preparing the compounds of formula (I).

Accordingly, this invention provides a process for preparing a compound of formula I which comprises:

a) reacting a compound of formula (II):

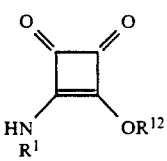
(II)

wherein $R^1$ is as defined above and $OR^{12}$ represents any alkoxy or aralkoxy leaving groups such as those having 1 to 6 and 7 to 12 carbon atoms, respectively, e.g. methoxy, ethoxy, benzyloxy, with a compound of formula (III):

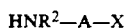
$HNR^2-A-X$     (III)

wherein $R_2$, A and X are as defined above or a salt or protected form thereof, if required removing any protecting group to give a compound of formula (I) wherein $R^2$ is as defined above if desired isolating as a pharmaceutically acceptable salt;

b) reacting a compound of formula (IV):

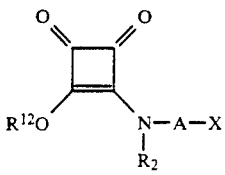
(IV)

wherein X, $R^2$ and $R^{12}$ are as defined above or a salt or protected form thereof with a compound of formula:

$H_2NR^1$     (V)

wherein $R^1$ is as defined above and removing any protecting group to give a corresponding compound of formula (I) or a salt thereof; or c) reacting a compound of formula (VI):

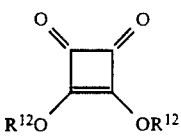
(VI)

wherein $R^{12}$ is as defined above and each is the same or different, with a compound of formula:

$H_2N-Z-NH-A-X$     (VII)

wherein X is as defined above or a salt or protected form thereof, Z and A are as defined above, if required removing any protecting group to give a corresponding compound having formula (I) wherein $R^1$ and $R^2$ taken together are Z, A and X are as defined above; or d) deprotecting, selectively if required, and cyclising a compound of the formula (VIII):

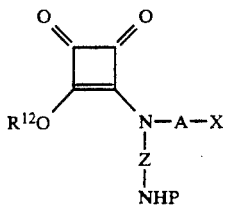
(VIII)

wherein X, Z, $R^{12}$ and A are as defined above or X may be -CN or a salt or protected form thereof, and P is an amino protecting group, which is preferably selectively removable if X is protected to give a corresponding compound having formula (I) where $R^1$ and $R^2$ are Z, if required also removing any protecting group on X; or e) reacting a compound of the formula (IX):

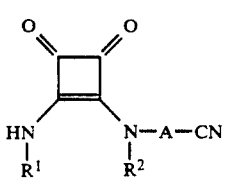
(IX)

wherein $R^1$, $R^2$ and A are as defined above, with an azide, such as an alkali metal azide, e.g. $NaN_3$ or tributyltin azide to give a corresponding compound of formula (I) where X is 5-tetrazolyl; or f) converting a compound of formula (I) wherein $R^3$, $R^4$ and $R^5$ are alkyl groups to give compounds of the formula (I) wherein $R^3$, $R^4$ and $R^5$ are hydrogen or salts thereof; or g) acidifying a salt of a compound of formula (I) to give the free acid or basifying an acid of formula (I) to give a salt thereof; or h) thermolysing a compound of the formula (X)

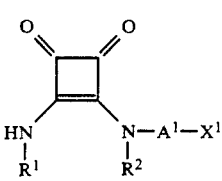
(X)

wherein $R^1$ is defined above, $X^1$ is $CO_2R^3$ or $-PO(OR^4)(OR^5)$ where $R^3$, $R^4$ and $R^5$ are all alkyl, 3,5-dioxo-1,2,4-oxadiazolidin-2-yl or protected 5-tetrazolyl, and $-A^1-$ represents alkylene of 2 to 6 carbon atoms substituted by a-$S(O)_m$-aryl radical where m represents 1 or 2, if required removing any protecting group to give a corresponding compound of formula (I) wherein A is alkenylene of 2 to 6 carbon atoms. Examples of aryl are univalent, aromatic hydrocarbons preferably having 7 to 12 carbon atoms, e.g. phenyl, tolyl, and the like.

As will be apparent to those skilled in the art, in some of the above mentioned reactions, where it is desired to prepare X as a carboxy or phosphoric acid, it may be necessary or advisable to protect such groups during the reaction or use a $C_1$-$C_6$ alkyl ester derivative thereof, e.g. t-butyl ester, followed by its removal. Examples of carboxy protecting groups are benzyl esters or esters of 7 or more carbon atoms.

Similarly, when X is 5-tetrazolyl, this group may be protected by standard means, e.g. using a trityl protecting group which is removable by acidification or hydrogenation. In addition, when $R^6$, $R^8$ or $R^{10}$ are hydroxy, appropriate protection during the reaction may be effected with the actyl, benzoyl, t-butyl, trityl, and preferably the benzyl group.

With regard to process a), the displacement of an alkoxy or aralkoxy substituent from the compound of formula (II) may be conveniently carried out in the absence of presence of base such as an alkali metal hydroxide (e.g. NaOH) with or without heating in the presence of an inert solvent such as ethanol. When X is an acidic moiety in the compound of formula (III) under basic reaction conditions, the product will be a salt which can be isolated as such or converted to the free acid by acidification. When X is a carboxylic acid function it may be protected, e.g. in the form of an ester or as a salt with a cation.

With regard to process b), the displacement of the $OR^{12}$ group may be carried out using ammonia or an amine of formula $H_2NR^2$ in the presence of an inert solvent such as ethanol with or without heating, the group X being protected if required.

With regard to process c), bicyclic compounds of formula I may be prepared by carrying out two displacement reactions using a diamine of formula VII preferably by heating an inert solvent such as ethanol. If the nitrogen is protected, the reaction may be carried out in two steps via an intermediate of formula (VIII) followed by deprotection and cyclisation as described in process d). Examples of amino protecting groups are benzyloxycarbonyl and substituent derivatives thereof removable by hydrogenation.

Process e) may be carried out using an alkali metal azide in an inert solvent such as dimethyl formamide in the presence of ammonium chloride with heating if necessary. When tributyltin azide is used, then the reaction may be carried out in an inert solvent such as toluene followed by acidification.

With regard to process f), when any of $R^3$ or $R^4$ and $R^5$ are alkyl groups, these may be removed by hydrolysis or other known methods to give the corresponding free acids or salts thereof.

Thermolysis of the compounds of formula X may be carried out by heating in an inert high boiling solvent such as toluene in the presence of sodium bicarbonate in order to produce compounds of formula I where A is alkenylene. Similarly, this process may be used to prepare starting materials used in the processes above where it is desired to prepare compounds wherein A represents alkenylene.

This invention also provides intermediates for preparing compounds of the formula (I). These intermediates include compounds having formulae (IV), (VIII) as shown and defined hereinabove and also intermediates to compounds of formula (IX) which intermediates having the formula (XI):

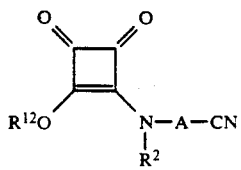

(XI)

The intermediates may be represented by the single general formula (XII):

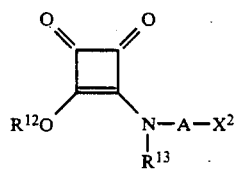

(XII)

or a salt thereof, where $X^2$ represents CN, $COOR^{14}$ where $R^{14}$ is hydrogen, alkyl of 1 to 6 carbon atoms or a carboxyl protecting group, $-PO(OR^{15})(OR^{16})$ where $R^{15}$ and $R^{16}$ are hydrogen or alkyl of 1 to 6 carbon atoms, 3,5-dioxo-1,2,4-oxadiazolidinyl or optionally protected 5-tetrazolyl, $R^{12}$ and A are as defined above, and $R^{13}$ represents hydrogen, alkyl of 1 to 6 carbon atoms, alkenyl of 2 to 6 carbon atoms, phenylalkyl of 7 to 12 carbon atoms or $-Z-NHP$ wherein, P is an amino protecting group and Z is hereinbefore defined.

Also included in this invention is a process for preparing the intermediates of formula (XII) which process comprises reacting a compound of formula (VI) as defined above, with a compound of the formula:

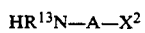

$HR^{13}N-A-X^2$ (XIII)

where A, $R^{13}$ and $X^2$ are as defined above, to give a corresponding compound of the formula (XII), or N-alkylating a compound of formula:

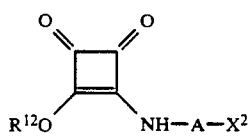

where $R^{12}$, A and $X^2$ are as defined above in the presence of a strong base, e.g. NaH, with a compound of formula $R^2$-halo where halo is a halogen such as chlorine or bromine and $R^2$ is as defined above except hydrogen to give a corresponding compound of formula (XII).

Starting materials used in any of the above mentioned processes for preparing the final products and intermediates are known compounds or can be prepared by analogous methods for known compounds.

The compounds of this invention are produced by conventional methods involving (1) the displacement of the alkoxy substituent of 3-amino-4-alkoxy-3-cyclobutene-1,2-dione with an amino acid ($H_2NAX$) in the presence of an equivalent weight of sodium hydroxide to obtain derivatives in which $R^2$ is hydrogen; (2) reacting 3,4-dialkoxy-3-cyclobutene-1,2-dione with an amine ($H_2NR^2$) followed by N-alkylation with the desired t-butylhalocarboxylate (halo$ACO_2$-t-butyl) in dimethyl formamide employing sodium hydride as the base, followed by displacement of the remaining alkoxy substituent with the desired amine ($H_2NR^1$) and deprotection of the t-butyl ester with an acid such as formic acid; and (3) in an analogous manner, 3,4-dialkoxy-3-cyclobutene-1,2-dione may be reacted with the desired amino acid ($H_2N$-A-$PO_3Et_2$) to displace one alkoxy group, and that intermediate may be N-alkylated in dimethylformamide with the desired alkyl halide ($R^2$ halo) in the presence of sodium hydride and/or the other alkoxy substituent can be displaced with the desired amine ($H_2NR^1$). The resulting phosphonate ester is converted to the free acid with bromotrimethylsilane. Employing a diamine such as $H_2N-(CH_2)_n-NHCH_2CH_2PO_3Et_2$ (n=2-4) with 3,4-diethoxy-3-cyclobutene-1,2-dione affords the dioxodiazabicycloethyl phosphonic acid esters such as is illustrated in Example 7, infra. The phosphonate ester is converted to the free acid conventionally. The initial diamine reactants are prepared by reacting N-protected alkylene diamines with (2-oxoethyl)phosphonic acid diethyl ester in the presence of sodium cyanoborohydride in methanol at a pH ~6.5 followed by removal of the N-protecting group, such as benzyloxycarbonyl, by hydrogenation.

Also, (4) the initial mono protected diamine phosphonate reactants are prepared by reacting N-protected alkylene diamines with $Br-A-PO_3Et_2$ in the presence of sodium carbonate in ethanol. The monoprotected diamine phosphonate such as (protecting group)—NH—$(CH_2)_n$—NH—A—$PO_3Et_2$ (n=2-4) is reacted with 3,4-dialkoxy-3-cyclobutene-1,2-dione to displace one alkoxy group. Removal of the benzyloxycarbonyl N-protecting group by hydrogenation or the t-butyloxycarbonyl N-protecting group by formic acid treatment leads to cyclization. The resulting dioxodiazabicycloalkylphosphonic acid esters are hydrolyzed to the free acid with bromotrimethylsilane; (5) the mono N-benzyloxycarbonyl diamine may be alkylated with Br—A—$CO_2$—t—Bu in the presence of diisopropylethylamine in dimethylformamide. The intermediate CBZ—NH—$(CH_2)_n$—NH—A—$CO_2$—t—Bu is reacted with 3,4-dialkoxy-3-cyclobutene-1,2-dione to displace one alkoxy group. Removal of the N-protecting group by hydrogenation of the intermediate leads to cyclization. The t-butyl group is cleaved by formic acid treatment to give the free acid; and (6) the mono N-t-butyloxycarbonyl diamine may be alkylated with Br—A—CN in the conventional manner. The intermediate BOC—NH—$(CH_2)_n$—NH—A—CN is reacted with 3,4-dialkoxy-3-cyclobutene-1,2-dione to displace one alkoxy group. Removal of the N-protecting group by formic acid treatment leads to cyclization. The nitrile is converted to the tetrazole by heating with sodium azide and ammonium chloride in dimethylformamide. When the alkylene bridge of the diamine contains a hydroxyl group, it is optionally O-protected throughout the reaction.

In all of the above reactions, the reactants are either known, commercially available or readily prepared by methods well within the skill of the medicinal chemist.

The compounds of the invention may contain one or more asymmetric carbon atoms (e.g. when any of $R^{6-10}$ is alkyl or any of $R^6$, $R^8$ and $R^{10}$ is hydroxyl), so that the compounds can exist in different stereoisomeric forms. All stereoisomeric forms are included within the invention. Such compounds can be, for example, racemates of optically active forms. The optically active forms can be obtained by resolution of the racemates or by asymmetric synthesis.

The following examples illustrate, without limitation, the preparation of representative compounds of this invention:

EXAMPLE 1

N-(2-Amino-3,4-dioxo-1-cyclobuten-1-yl)beta-alanine

A solution of 3-amino-4-ethoxy-3-cyclobutene-1,2-dione (2.0 g, 14 mmol) in ethanol (100 mL) was treated with β-alanine (1.26 g, 14 mmol) dissolved in 1 N sodium hydroxide solution (14 mL, 14 mmol). After 5.5 hours at room temperature, the resulting yellow solid was filtered, washed with ethanol, and concentrated under high vacuum to yield the pure title compound as the sodium salt, hemihydrate (2.6 g, 86% of theory, m.p. 280°-282° C.); IR (KBr, cm$^{31\ 1}$): 1810; MS (-FAB) 205 (M-H, 13) 183 (M-Na, 44), 175 (17), 148 (100); $^1$H NMR ($D_2O$, 400 MHz): δ3.59 (br s, 2H), 2.31 (t,J=6 Hz, 2H); $^{13}$C NMR ($D_2O$, 400 MHz): ppm 182.01, 181.61, 179.30, 168.94, 168.54, 41.18, 37.97.

Elemental analysis for $C_7H_7NaN_2O_4.\frac{1}{2}H_2O$: Calc'd: C, 39.08; H, 3.75; N, 13.02. Found: C, 38.78; H, 3.48; N, 12.86.

a) In the same manner, condensing stoichiometric amounts of 3-amino-4-ethoxy-3-cyclobutene-1,2-dione with ethyl glycinate produces N-(2-amino-3,4-dioxo-1-cyclobutenyl)glycine ethyl ester, m.p. 231°-233° C.

Elemental analysis for $C_8H_{10}N_2O_4$: Calc'd: C, 48.49; H, 5.09; N, 14.14. Found: C, 48.40; H, 4.90; N, 14.02.

b) The substitution of glycine for β-alanine in the procedure of Example 1 yields N-(2-amino-3,4-dioxo-1-cyclobutenyl)glycine as the sodium salt, 4/3 $H_2O$, m.p. 210°-215° C. (dec.).

Elemental analysis for $C_6H_5NaN_2O_4.4/3\ H_2O$: Calc'd: C, 33.34; H, 3.58; N, 12.96. Found: C, 33.36; H, 3.26; N, 13.12.

c) Similarly, the substitution of 4-aminobutanoic acid for β-alanine in the procedure of Example 1 affords 4-[(2-amino-3,4-dioxo-1-cyclobutenyl)amino]butanoic acid as the sodium salt, partial hydrate, m.p. 240°-243° C. (dec.).

Elemental analysis for $C_8H_9NaN_2O_4.0.58\ H_2O$: Calc'd: C, 41.67; H, 4.44; N, 12.15. Found: C, 41.27; H, 4.04; N, 12.03.

EXAMPLE 2

2-[2-[(2-Amino-3,4-dioxo-1-cyclobuten-1-yl)amino]ethyl]-1,2,4-oxadiazolidine-3,5-dione A solution of 3-amino-4-ethoxy-3-cyclobutene-1,2-dione (0.56 g, 4.0 mmol) in ethanol (20 mL) was added to 2-(2-aminoethyl)-1,2,4-oxadiazolidine-3,5-dione hydrobromide (0.90 g, 4.0 mmol) in ethanol (100 mL). The reaction mixture was treated with 1N sodium hydroxide solution (8 mL, 8 mmol) and allowed to stir for 24 hours at room temperature. The resulting precipitate was filtered, dissolved in water and passed through an ion exchange column (AG 50W-X2, 100-200 mesh, H$^+$ form), eluting with water. The eluent was freeze dried yielding the title compound as a cream colored solid, partial hydrate (0.45 g, 45%, mp 225° C. (dec)); IR (KBr, cm$^{-1}$) 3300, 3140, 1820, 1740, 1720, 1640; MS (+FAB) 242 (MH+); $^1$H NMR (DMSO, 400 MHz): δ 12.4 (br s, NH), 7.5 (br s, 3 NH), 4.0-3.5 (m, 4H); $^{13}$C NMR (DMSO, 400 MHz): ppm 183.72, 183.63, 170.06, 168.96, 158.17, 152.72, 50.41, 41.68.

Elemental analysis for $C_8H_8N_4O_5.0.45\ H_2O$; Calc'd: C, 38.70; H, 3.61; N, 22.56. Found: C, 39.10; H, 3.24; N, 22.19.

a) The same reaction conditions as illustrated in Examples 1 and 2 applied to β-alanine and 4-ethoxy-3-methylamino-3-cyclobutene-1,2-dione provides N-[2-(methylamino)-3,4-dioxo-1-cyclobutenyl]beta-alanine as the sodium salt, ¼ $H_2O$, m.p. 310° C. (dec.).

Elemental analysis for $C_8H_9NaN_2O_4.\frac{1}{4}\ H_2O$ Calc'd: C, 42.77; H, 4.26; N, 12.47. Found: C, 42.77; H, 3.88; N, 12.53.

b) Similarly, 3-benzylamino-4-ethoxy-3-cyclobutene-1,2-dione when reacted with β-alanine produces 3-[[3,4-dioxo-2[(phenylmethyl)amino]-1-cyclobutenyl]amino]- propanoic acid as the sodium salt, ½ H₂O, m.p. 298°-302° C. (dec.).

Elemental analysis for C₁₄H₁₃NaN₂O₄.½ H₂O; Calc'd: C, 55.08; H, 4.62; N, 9.18. Found: C, 54.74; H, 4.53; N, 9.06.

EXAMPLE 3

N-(2-Amino-3,4-dioxo-1-cyclobuten-1-yl)-N-(2-propenyl)glycine

A solution of 3,4-diethoxy-3-cyclobutene-1,2-dione (5.2 g, 31 mmol) in ethanol (80 mL) was treated at room temperature with allylamine (2.3 mL, 31 mmol), which was dissolved in ethanol (40 mL), over a 2 hour period. The reaction mixture was concentrated in vacuo to afford crude 1-(2-propenylamino)-2-ethoxy-3,4-dioxo-1-cyclobutene as a light yellow solid (5.6 g). The crude intermediate was dissolved in anhydrous dimethylformamide (50 mL) and added dropwise to a suspension of 60% sodium hydride (1.5 g, 37 mmol) in anhydrous dimethylformamide (50 mL) under nitrogen. The anion was quenched with t-butyl bromoacetate (6.0 mL, 37 mmol) and the reaction mixture was stirred for 1.5 hours, poured into water (500 mL), extracted with ethyl acetate (2×200 mL), and dried (MgSO₄) to yield N-(2-ethoxy-3,4-dioxo-1-cyclobuten-1-yl)-N-(2-propenyl)glycine 1,1-dimethylethyl ester. Purification was achieved by flash chromatography (10 cm diameter, elution with 20% ethyl acetate in petroleum ether) affording a yellow oil (4.56 g, 50%); ¹H NMR (CDCl₃, 300 MHz): δ 5.88-5.72 (m, 1H), 5.35-5.22 (m, 2H), 4.80-4.68 (m, 2H), 4.35, 4.08 (d, J=7 Hz, 2H), 4.28, 3.95 (s, 2H), 1.48 (s, 9H), 1.45 (t, J=7 Hz, 3H).

Ethanolic ammonia (25 mL) was added to a flask containing N-(2-ethoxy-3,4-dioxo-1-cyclobuten-1-yl)-N-(2-propenyl)glycine 1,1-dimethylethyl ester (2.5 g, 8.5 mmol) at room temperature. After 5 hours the reaction mixture was concentrated and purified by flash chromatography (5 cm diameter, elution with 5% methanol in dichloromethane) to yield N-(2-amino-3,4-dioxo-1-cyclobuten-1-yl)-N-(2-propenyl)glycine 1,1-dimethylethyl ester as a white solid (1.6 g, 71%, mp 175°-176° C.); IR (KBr, cm⁻¹): 3300, 3140, 1810, 1740, 1670, 1650; MS (EI): 266 (M⁺, 34), 210 (24), 165 (100), 109 (54), 95 (89), 68 (68); ¹H NMR (DMSO, 400 MHz): δ 7.70 (br s, NH₂), 5.84-5.77 (m, 1H), 5.26 (d, J=17 Hz, 1H), 5.19 (d, J=10 Hz, 1H), 4.3-4.0 (br m, 4H), 1.39 (s, 9H).

Deprotection of N-(2-amino-3,4-dioxo-1-cyclobuten-1-yl)-N-(2-propenyl)glycine 1,1-dimethyl ethyl ester (1.6, 6.0 mmol) was performed by stirring in formic acid (20 mL) for 24 hours. The reaction mixture was concentrated, azeotroped with dichloromethane and recrystallized with difficulty (oiled out several times) to afford the title compound, ¼ hydrate, as an off-white solid (0.80 g, 62%, mp 172°-175° C.); IR (KBr, cm⁻¹): 3330, 3180, 1810, 1720, 1640; MS(EI): 210 (M⁺, 75), 165 (34), 109 (41), 95 (100 ), 68 (63); ¹H NMR (DMSO, 400 MHz): δ 12.94 (br s, OH), 7.70 (s, NH₂), 5.86-5.77 (m, 1H), 5.26 (d, J=17 Hz, 1H), 5.19 (d, J=10 Hz, 1H), 4.3-4.0 (br m, 4H).

Elemental analysis for C₉H₁₀N₂O₄.¼ H₂O: Calc'd: C, 50.35; H, 4.93; N, 13.05. Found: C, 50.13; H, 4.82; N, 12.86.

a) Following the procedure of Example 3, with the exception that 2-methylallylamine is employed as the initial reactant, affords N-(2-amino-3,4-dioxo-1-cyclobutenyl)-N-(2-methyl-2-propenyl)glycine, m.p. 184°-186° C.

Elemental analysis for C₁₀H₁₂N₂O₄.0.1 H₂O: Calc'd: C, 53.14; H, 5.44; N, 12.39. Found: C, 53.09; H, 5.38; N, 12.16.

b) Similarly, employing benzylamine as the initial reactant, the procedure of Example 3 affords N-(2-amino-3,4-dioxo-1-cyclobutenyl)-N-(phenylmethyl)glycine, m.p. 177°-179° C.

Elemental analysis for C₁₃H₁₂N₂O₄: Calc'd: C, 60.00; H, 4.65; N, 10.76. Found: C, 59.74; H, 4.60; N, 10.61.

EXAMPLE 4

[2-[(2-Amino-3,4-dioxo-1-cyclobuten-1-yl)amino]ethyl]phosphonic acid

To a solution of 3,4-diethoxy-3-cyclobutene-1,2-dione (4.00 g, 23.5 mmol) in ethanol (100 mL) was added 2-aminoethylphosphonic acid diethyl ester (5.43 g, 30.0 mmol) in ethanol (100 mL) over a 1 hour period. After leaving overnight the reaction mixture was preadsorbed onto silica gel and purified by flash chromatography (5.5 cm diameter, gradient elution with 2.5-10% isopropanol in dichloromethane) to yield [2-[(2-ethoxy-3,4-dioxo-1-cyclobuten-1-yl)amino]ethyl]phosphonic acid diethyl ester as an oil which solidifies on standing (3.98 g, 55%, mp 66°-68° C.); IR (KBr, cm⁻¹): 3400, 3180, 1800, 1700, 1600; MS (+FAB): 306 (MH⁺, 100), 278 (14), 137 (14), 109 (35); ¹H NMR (CDCl₃, 400 MHz): δ6.58, 6.46 (br s, NH), 4.75 (br m, 2H), 4.21-4.07 (m, 4H), 4.00, 3.75 (br m, 2H), 2.08 (d of t, J=17.5 and 6.5 Hz, 2H), 1.46 (br m, 3H), 1.35 (t, J=7 Hz, 6H).

A solution of [2-[(2-ethoxy-3,4-dioxo-1-cyclobuten-1-yl)amino]ethyl]phosphonic acid diethyl ester (1.69 g, 5.5 mmol) in 100% ethanol (40 mL) was placed in flask equipped with an addition funnel and a nitrogen inlet. Saturated ethanolic ammonia (190 mL) was placed in the addition funnel and added dropwise over 1 hour. The reaction mixture was left stirring at room temperature for a total of 24 hours and then concentrated in vacuo. The resulting solid was recrystallized from methanol in ethyl acetate to afford [2-[(2-amino-3,4-dioxo-1-cyclobuten-1-yl)amino]ethyl]phosphonic acid diethyl ester as a yellow solid (1.27 g, 82%, mp=150°-152° C. dec); IR (KBr, cm⁻¹): 1805, 1650; MS (+FAB): 277 (MH⁺, 100), 182 (20), 109 (15); ¹H NMR (DMSO, 400 MHz): δ 7.5 (br s, 3 NH), 4.1-3.9 (m, 4H), 3.7-3.6 (m, 2H), 2.11 (d of t, J=17.5 and 7.5 Hz, 2H), 1.22 (t, 6H).

Elemental analysis for C₁₀H₁₇N₂O₅P.1/5 H₂O Calc'd: C, 42.92; H, 6.27; N, 10.01. Found: C, 42.90; H, 6.05; N, 10.00.

A suspension of [2-[(2-amino-3,4-dioxo-1-cyclobuten-1-yl)amino]ethyl]phosphonic acid diethyl ester one fifth hydrate (0.90 g, 3.2 mmol) in dry 1,2-dichloroethane (47 mL) was placed in a flask which was equipped with a reflux condenser and which had previously been evacuated and placed under nitrogen. Bromotrimethylsilane (2.6 mL, 19.8 mmol) was added to the flask via syringe, and the reaction mixture was refluxed for 10 minutes. The mixture was then concentrated in vacuo to produce a rust colored solid which was dissolved in deionized water (80 mL). The water was washed with diethyl ether (2×100 mL) and concentrated in vacuo. The resulting rust colored solid was recrystallized from methanol and water in ethylacetate to produce the title compound as a dark yellow solid (0.360 g, 50%, mp=230°-239° C. dec.); IR (KBr, cm⁻¹): 1790; ¹H NMR (DMSO, 400 MHz): δ 7.5 (br s, 3NH), 3.67 (br s, 2H), 1.85 (d of t, J=17.5 and 7.5 Hz, 2H).

Elemental analysis for $C_6H_9N_2O_5P.1/5\ H_2O$ Calc'd: C, 32.21; H, 4.24; N, 12.52. Found: C, 32.20; H, 4.00; N, 12.46.

a) Following the procedure of Example 4, with the exception that aminomethylphosphonic acid diethyl ester was employed as the reactant, gives [[(2-amino-3,4-dioxo-1-cyclobutenyl)amino]methyl]phosphonic acid as a three quarter hydrate, m.p. 200°-250° C. (dec.).

Elemental analysis for $C_5H_7N_2O_5P.\frac{3}{4}\ H_2O$ Calc'd: C, 27.35; H, 3.90; N, 12.76. Found: C, 27.72; H, 3.39; N, 12.39.

b) Again, employing 3-aminopropylphosphonic acid diethyl ester as the reactant in the process of Example 4 gives [3-[(2-amino-3,4-dioxo-1-cyclobuten-1-yl)amino]propyl]phosphonic acid, m.p. 220°-230° C. (dec.).

Elemental analysis for $C_7H_{11}N_2O_5P$: Calc'd: C, 35.91; H, 4.74; N, 11.96. Found: C, 35.94; H, 4.57; N, 11.76.

c) With 4-aminobutylphosphonic acid diethyl ester as the reactant in the process of Example 4, [4-[(2-amino-3,4-dioxo-1-cyclobuten-1-yl)amino]butyl]phosphonic acid 0.25 hydrate is obtained as the product, m.p. 220°-242° C. (dec.).

Elemental analysis for $C_8H_{13}N_2O_5P.\frac{1}{4}\ H_2$: Calc'd: C, 38.03; H, 5.38; N, 11.09. Found: C, 38.09; H, 5.01; N, 11.09.

EXAMPLE 5

[(E)-4-[(2-Amino-3,4-dioxo-1-cyclobuten-1-yl)amino]-2-butenyl]phosphonic acid

A nitrogen blanketed solution of [(E)-4-(N-phthalimido)-2-buten-1-yl]phosphonic acid diethyl ester (8.58 g, 25.4 mmol) prepared by the method of Connel et al., *J. Org. Chem.*, 54, 3359 (1989) in ethanol (75 mL) was treated with 85% hydrazine hydrate (5 mL) and brought to reflux for 15 minutes. The virtually solid reaction mixture was concentrated and partitioned between 2.5N sodium hydroxide solution (250 mL) and dichloromethane (150 mL) with stirring for 30 minutes. After separating, the aqueous layer was again extracted with dichloromethane (2×150 mL) and the combined organic layers were dried ($Na_2SO_4$) and concentrated to afford [(E)-4-amino-2-buten-1-yl]phosphonic acid diethyl ester (5.32 g, 25 mmol); this material was dissolved in ethanol (100 mL) and added over 1.5 hours to ethanolic (100 mL) 3,4-diethoxy-3-cyclobutene-1,2-dione (4.32 g, 25.4 mmol). After leaving overnight, the reaction mixture was concentrated and purified by flash chromatography (7.5 cm diameter, elution with 3% methanol in dichloromethane) to yield [(E)-4-[(2-ethoxy-3,4-dioxo-1-cyclobuten-1-yl)amino]-2-butenyl]phosphonic acid diethyl ester as a light yellow oil (7.15 g, 85%); $^1$H NMR (CDCl$_3$, 200 MHz): δ 6.5 (br, s, NH), 5.75-5.66 (m, 2H), 4.77 (q,J=7 Hz, 2H), 4.23 (br s, 2H), 4.2-4.0 (m, 4H), 2.61 (d of d,J=22 and 7 Hz, 2H), 1.46 (t,J=7 Hz, 3H), 1.33 (t,J=7 Hz, 6H).

Ethanolic ammonia (235 mL) was combined with [(E)-4-[(2-ethoxy-3,4-dioxo-1-cyclobuten-1-yl)amino]-2-butenyl]phosphonic acid diethyl ester (7.15 g, 21.6 mmol) and the solution was left stirring for 3 days and then evaporated. Recrystallization from methanol in ethyl acetate removed a yellow impurity, but flash chromatography (7.5 cm diameter, elution with 5% methanol in dichloromethane) was required to eliminate a more polar contaminant. Recrystallization of this material with methanol in ethyl acetate (final volume=200 mL) afforded [(E)-4-[(2-amino-3,4-dioxo-1-cyclobuten-1-yl)amino]-2-butenyl]phosphonic acid diethyl ester as a flocculant white solid (4.43 g, 68%, mp 145°-147° C.); IR (KBr, cm$^{-1}$): 3280, 3100, 1800, 1640; MS (+FAB): 303 (MH$^+$, 100), 135 (62); $^1$H NMR (DMSO, 400 MHz): δ 7.5 (br s, 3NH), 5.74-5.68 (m, 1H), 5.57-5.48 (m, 1H), 4.09 (br s, 2H), 4.02-3.91 (m, 4H), 2.64 (d of d, J=21.5 and 7 Hz, 2H), 1.19 (t,J=7 Hz, 6H).

Elemental analysis for $C_{12}H_{19}N_2O_5P$: Calc'd: C, 47,68; H, 6.34; N, 9.27. Found: C, 47.46; H, 5.95; N, 9.21.

A solution of [(E)-4-[(2-amino-3,4-dioxo-1-cyclobuten-1-yl)amino]-2-butenyl]phosphonic acid diethyl ester (1.0 g, 3.3 mmol) and bromotrimethylsilane (4.6 mL, 35 mmol) in anhydrous 1,2-dichloroethane (30 mL) under nitrogen was refluxed for 20 minutes, and then cooled and evaporated. The residue was dissolved in water (150 mL) and washed with diethyl ether (2×75 mL). The resulting material, upon concentrating the aqueous layer, was recrystallized from methanol in ethyl acetate (final volume=100 mL) to yield [(E)-4-[(2-amino-3,4-dioxo-1-cyclobuten-1-yl)amino]-2-butenyl]phosphonic acid one third hydrate as a yellow solid (0.59 g, 71%, mp 220°-230° C. (dec)); IR (KBr, cm$^{-1}$): 3280, 3100, 1800, 1640; MS (-FAB): 245 (M-H); $^1$H NMR (DMSO, 400 MHz): δ 7.47 (br s, 3 NH), 5.63-5.58 (m, 2H), 4.10 (br s, 2H), 2.38 (d of d, J=21 and 6 Hz, 2H).

Elemental analysis for $C_8H_{11}N_2O_5P.\frac{1}{3}\ H_2O$: Calc'd: C, 38.11; H, 4.66; N, 11.11. Found: C, 38.10; H, 4.46; N, 11.00.

EXAMPLE 6

[2-[(2-Amino-3,4-dioxo-1-cyclobuten-1-yl)methylamino]ethyl]phosphonic acid

A cold (0° C.) suspension of 60% sodium hydride (500 mg, 12.5 mmol) in anhydrous dimethylformamide (15 mL) under nitrogen was treated with a solution of [2-[(2-ethoxy-3,4-dioxo-1-cyclobuten-1-yl)amino]ethyl]phosphonic acid diethyl ester (3.23 g, 10.6 mmol), prepared as in Example 4, in dimethylformamide (20 mL) over 30 minutes. Iodomethane (0.78 mL, 12.5 mmol) was introduced and the ice bath was removed for 30 minutes and then reapplied for introduction of 1N hydrochloric acid solution (20 mL). The reaction mixture was poured into water (200 mL), extracted with dichloromethane (2×200 mL), dried (MgSO$_4$), and concentrated under high vacuum (1 mm) at 40° C. The crude material was purified by flash chromatography (7.5 cm diameter, elution with 2.5% methanol in dichloromethane) to afford [2-[(2-ethoxy-3,4-dioxo-1-cyclobuten-1-yl)methylamino]ethyl]phosphonic acid diethyl ester as an oil (3.00 g, 89%); IR (neat, cm$^{-1}$) 1805, 1715, 1620; MS (+FAB): 320 (MH$^+$, 100), 109 (20); $^1$H NMR (CDCl$_3$, 400 MHz): δ 4.78-4.74 (m, 2H), 4.16-4.09 (m, 4H), 3.94, 3.68 (m, 2H), 3.35, 3.19 (s, 3H), 2.15-2.09 (m, 2H), 1.48-1.44 (m, 3H), 1.34 (t, J=7 Hz, 6H).

An ethanolic solution (40 mL) of [2-[(2-ethoxy-3,4-dioxo-1-cyclobuten-1-yl)methylamino]ethyl]phosphonic acid diethyl ester (3.00 g, 9.40 mmol) was combined with ethanolic ammonia solution (70 mL) and left for 18 hours. After concentrating in vacuo, the solid was recrystallized twice from methanol in ethyl acetate (final volume=50 mL) to yield [2-[(2-amino-3,4-dioxo-1-cyclobuten-1-yl)methylamino]ethyl]phosphonic acid diethyl ester as a solid (2.10 g, 77%, mp 130°-132° C.); IR (KBr, cm$^{-1}$): 3320, 3160, 1800, 1670, 1650, 1640; MS (+FAB): 291 (MH$^+$, 100), 196 (22), 109 (20); $^1$H NMR (DMSO, 400 MHz): δ 7.61 (br s NH$_2$), 4.02-3.94 (m, 4H), 3.74 (br s, 2H), 3.13 (br s, 3H), 2.13 (d of t, J=18 and 7.5 Hz, 2H), 1.22 (t,J=7 Hz, 6H).

Elemental analysis for $C_{11}H_{19}N_2O_5P$: Calc'd: C, 45.52; H, 6.60; N, 9.65. Found: C, 45.41, H, 6.55, N, 9.65.

A suspension of [2-[(2-amino-3,4-dioxo-1-cyclobuten-1-yl)methylamino]ethyl]phosphonic acid diethyl ester (600 mg, 2.3 mmol) in anhydrous 1,2-dichloroethane (20 mL) under nitrogen was treated with bromotrimethylsilane (2.0 mL, 15 mmol) and heated to reflux for 10 minutes. The yellow solution was concentrated and the resulting solid was dissolved in water (75 mL), washed with diethyl ether (2×50 mL) and evaporated. The solid was dissolved in boiling methanol, filtered, and concentrated with the addition of ethyl acetate to a final volume of 75 mL to afford the title compound as a yellow solid (310 mg, 58%, mp 230°-260° C. dec); IR (KBr, cm$^{-1}$): 3340, 1800; MS (−FAB): 233 (M-H, 32), 148 (100); $^1$H NMR (DMSO, 400 MHz): δ 7.62 (br s, NH$_2$), 3.68 (br s, 2H), 3.16 (br s, 3H), 1.90 (d of t,J=18 and 7.5 Hz, 2H).

Elemental analysis for $C_7H_{11}N_2O_5P$: Calc'd: C, 35.91; H, 4.74; N, 11.96. Found: C, 35.52, H, 4.79; N, 11.83.

a) Following the procedure in Example 6, with the exception that aminomethylphosphonic acid diethyl ester is employed as the initial reactant gives [[(2-amino-3,4-dioxo-1-cyclobuten-1-yl)methylamino]methyl]phosphonic acid, m.p. 245°-250° C. (dec).

Elemental analysis for $C_6H_9N_2O_5P$: Calc'd: C, 32.74; H, 4.12; N, 12.73. Found: C, 32.62; H, 4.15; N, 12.87.

EXAMPLE 7

[2-(7,8-Dioxo-2,5-diazabicyclo[4.2.0]oct-1(6)-en-2-yl)ethyl]phosphonic acid

A solution of (2-aminoethyl)carbamic acid phenylmethyl ester (3.06 g, 16 mmol), (2-oxoethyl)phosphonic acid diethyl ester (2.88 g, 16 mmol) and sodium cyanoborohydride (1.00 g, 16 mmol) in dry methanol (90 mL) was prepared under nitrogen. Methanolic hydrogen chloride was added until the solution remained slightly acidic (pH 6.5). After 3 hours, additional sodium cyanoborohydride (0.25 g, 4.0 mmol) was introduced and the reaction was left overnight. After acidifying to pH 1.5 with concentrated hydrochloric acid, the methanol was removed in vacuo and the residue was diluted with water (25 mL). After washing with diethyl ether (3×25 mL), the aqueous layer was basified to pH 10 with 1N sodium hydroxide solution, saturated with solid sodium chloride, and then extracted with chloroform (3×50 mL). The dried (Na$_2$SO$_4$) organic layer was preadsorbed onto silica gel and purified by flash chromatography (3 cm diameter, gradient elution with 5–10% methanol in dichloromethane) to yield [2-[[2-(diethoxyphosphinyl)ethyl]amino]ethyl]carbamic acid phenylmethyl ester as a pale yellow oil (2.90 g, 51%); IR (neat, cm$^{-1}$): 3300, 1715; MS (+FAB): 359 (MH+, 100), 91 (70); $^1$H NMR (CDCl$_3$, 400 MHz): δ 7.36 (m, 5H), 5.46 (br s, NH), 5.10 (s, 2H), 4.16–4.02 (m, 4H), 3.29 (q, J=5.5 Hz, 2H), 2.89 (d of t, J=17 and 7 Hz, 2H), 2.75 (t, J=5.5 Hz, 2H), 1.95 (d of t, J=18 and 7 Hz, 2H), 1.82 (br s, NH), 1.31 (t, J=7 Hz, 6H).

Elemental analysis for $C_{16}H_{27}N_2O_5P.4/5$ H$_2$O: Calc'd: C, 51.55; H, 7.73; N, 7.51. Found: C, 51.69; H, 7.83; N, 7.53.

To a flask containing 10% palladium on carbon (3.79 g) under nitrogen was added [2-[[2-diethoxyphosphinyl)ethyl]amino]ethyl]carbamic acid phenylmethyl ester (3.79 g, 10 mmol) in ethanol (50 mL), followed by 1,4-cyclohexadiene (10.4 mL, 110 mmol). After stirring the suspension overnight, it was filtered through Celite ®, preadsorbed onto silica gel, and purified by flash chromatography (7 cm diameter, elution with dried (MgSO$_4$) 5/10/85 ammonium hydroxide/methanol/dichloromethane) to afford [2-[(2-aminoethyl)amino]ethyl]phosphonic acid diethyl ester as a yellow oil (1.98 g, 88%); MS (+FAB): 225 (MH+,9), 194 (100), 166 (34), 138 (71), 120 (38), 57 (39), 44 (32); $^1$H NMR (CDCl$_3$, 400 MHz): δ 4.18–4.04 (m, 4H), 2.91 (d of t, J=15 and 7 Hz, 2H), 2.80 (t, J=5.5 Hz, 2H), 2.68 (t, J=5.5 Hz, 2H), 1.98 (d of t, J=18 and 7 Hz, 2H), 1.68 (br s, 3 NH), 1.33 (t, J=7 Hz, 6H).

Solutions (10 mL each) of 3,4-diethoxy-3-cyclobutene-1,2-dione (1.27 mL, 8.6 mmol) and [2-[(2-aminoethyl)amino]ethyl]phosphonic acid diethyl ester (1.92 g, 8.6 mmol) in ethanol were injected separately via syringe pump into refluxing ethanol (22 mL) over 3 hours. After refluxing overnight, the red-brown solution was preadsorbed onto silica gel and purified by flash chromatography (7 cm diameter, gradient elution with 2.5–10% methanol in ethyl acetate) and recrystallization (methanol in ethyl acetate) to yield [2-(7,8-dioxo-2,5-diazabicyclo[4.2.0]oct-1-(6)-en-2-yl)ethyl]phosphonic acid diethyl ester as a beige solid (0.78 g, 30%, mp 115°-116° C.); IR (KBr, cm$^{-1}$): 3170, 1780, 1660; MS (+FAB): 303 (MH+, 100), 109 (38); $^1$H NMR (CDCl$_3$, 400 MHz): δ 7.64 (br s, NH), 4.16–4.06 (m, 4H), 3.80–3.73 (m, 2H), 3.63–3.60 (m, 2H), 3.48 (t, J=5 Hz, 2H), 2.31 (d of t, J=18 and 7.5 Hz, 2H), 1.33 (t, J=7 Hz, 6H).

Elemental analysis for $C_{12}H_{19}N_2O_5P$; Calc'd: C, 47.68; H, 6.34; N, 9.27. Found: C, 47.39; H, 6.32; N, 9.22.

A solution of [2-(7,8-dioxo-2,5-diazabicyclo[4.2.0]oct-1(6)-en-2-yl)ethyl]phosphonic acid diethyl ester (0.78 g, 2.6 mmol) and bromotrimethylsilane (2.1 mL, 16 mmol) in dry 1,2-dichloroethane (30 mL) was refluxed under nitrogen for 20 minutes. The cooled reaction mixture was concentrated in vacuo, and the residue was dissolved in water (100 mL) and washed with diethyl ether (3×50 mL). After concentrating the aqueous layer, the residue was recrystallized from water (25 mL) and methanol (300 mL) to yield a solid beige impurity which was removed by filtration. The filtrate was concentrated and recrystallized from water in isopropanol to yield the title compound as a yellow solid (0.37 g, 58%, mp 220°-270° C. dec); IR (KBr, cm$^{-1}$): 1800; MS (-FAB): 245 (M-H); $^1$H NMR (DMSO/drop of DCl, 400 MHz): δ 3.58–3.51 (m, 2H), 3.40–3.33 (m, 4H), 2.07–1.98 (m, 2H).

Elemental analysis for $C_8H_{11}N_2O_5P$: Calc'd: C, 39.04; H, 4.50; N, 11.38. Found: C, 38.60; H, 4.30; N, 11.11.

EXAMPLE 8

[2-(8,9-Dioxo-2,6-diazabicyclo[5.2.0]non-1(7)-en-2-yl)ethyl]phosphonic acid

A solution of (3-aminopropyl)carbamic acid phenylmethyl ester (6.11 g, 29 mmol), (2-oxoethyl)phosphonic acid diethyl ester (5.24 g, 29 mmol) and sodium cyanoborohydride (2.73 g, 43 mmol) in dry methanol (100 mL) was prepared under nitrogen. Methanolic hydrogen chloride was added until the solution remained slightly acidic (pH 6.5). After several hours the reaction was made acidic (pH 1.5) with concentrated hydrochloric acid, the methanol was removed in vacuo and the residue was diluted with water (25 mL). After washing with diethyl ether (3×30 mL), the aqueous layer was basified to pH 10 with 1N sodium hydroxide solution, saturated with solid sodium chloride, and then extracted with chloroform (3×30 mL). The dried (Na$_2$SO$_4$) organic layer was preadsorbed onto silica gel and purified by flash chromatography (7 cm diameter, gradient elution with 5-20% methanol in dichloromethane) to yield [3-[[2-(diethoxyphosphinyl)ethyl]amino]propyl]carbamic acid phenylmethyl ester as a waxy solid (3.86 g, 36%); IR (neat, cm$^{-1}$): 3300, 1720, 1250, 1030; MS (+FAB): 373 (MH$^+$, 100), 91 (90); $^1$H NMR (CDCl$_3$, 400 MHz): δ 7.36-7.29 (m, 5H), 5.58 (br s, NH), 5.09 (s, 2H), 4.15-4.04 (m, 4H), 3.29 (q, J=6 Hz, 2H), 2.91 (d of t, J=16 and 7 Hz, 2H), 2.71 (t, J=6 Hz, 2H), 1.98 (d of t, J=18 and 7 Hz, 2H), 1.70 (p, J=6 Hz, 2H), 1.31 (t, J=7 Hz, 6H).

A solution of [3-[[2-(diethoxyphosphinyl)ethyl]amino]propyl]carbamic acid phenylmethyl ester (3.17 g, 8.5 mmol) in absolute ethanol (40 mL) was added over 45 minutes to 3,4-diethoxy-3-cyclobutene-1,2-dione (2.3 mL, 16 mmol) dissolved ethanol (55 mL). After leaving overnight, the reaction mixture was preadsorbed onto silica gel and purified by flash chromatography (7 cm diameter, gradient elution was 2.5-10% methanol in dichloromethane) to yield [3-[[2-(diethoxyphosphinyl)ethyl](2-ethoxy-3,4-dioxo-1-cyclobuten-1-yl)amino]propyl]carbamic acid phenylmethyl ester as a viscous oil (3.75 g, 89%); $^1$H NMR (CDCl$_3$, 400 MHz): δ 7.35 (m, 5H), 5.45 (br m, NH), 5.09 (s, 2H), 4.80-4.71 (m, 2H), 4.16-4.09 (m, 4H), 3.90-3.48 (m, 4H), 3.23-3.20 (m, 2H), 2.16-2.05 (m, 2H), 1.85-1.79 (m, 2H), 1.47, 1.41 (t, J=7 Hz, 3H), 1.34 (t, J=7 Hz, 6H).

To a flask containing 10% palladium on carbon (2.11 g) under nitrogen was added [3-[[2-(diethoxyphosphinyl)ethyl](2-ethoxy-3,4-dioxo-1cyclobuten-1-yl)amino]propyl]carbamic acid phenylmethyl ester (2.11 g, 4.2 mmol) in absolute ethanol (180 mL), followed by 1,4-cyclohexadiene (4.3 mL, 45 mmol). After stirring for 5 hours, the reaction mixture was filtered through Celite ® and concentrated in vacuo to yield a crude solid, which was recrystallized from methanol and ethyl acetate (total volume=20 mL), filtered, and washed with hexane to afford [2-(8,9-dioxo-2,6-diazabicyclo[5.2.0]non-1(7)-en-2-yl)ethyl]phosphonic acid diethyl ester hemihydrate as a cream colored solid (0.82 g, 62%, mp 148°-149° C.); IR (KBr, cm$^{-1}$): 1810; $^1$H NMR (CDCl$_3$, 400 MHz): δ 7.50 (br s, NH), 4.18-4.10 (m, 4H), 4.09-4.00 (m, 2H), 3.51-3.46 (m, 4H), 2.19 (d of t, J=18 and 7.5 Hz, 2H), 2.10-2.04 (m, 2H), 1.34 (t, J=7 Hz, 6H).

Elemental analysis for C$_{13}$H$_{21}$N$_2$O$_5$P.½ H$_2$O: Calc'd: C, 47.99; H, 6.82; N, 8.61. Found: C, 48.23; H, 6.57; N, 8.52.

A solution of [2-(8,9-dioxo-2,6-diazabicyclo[5.2.0]-non-1(7)-en-2-yl)ethyl]phosphonic acid diethyl ester (1.41 g, 4.5 mmol) and bromotrimethylsilane (4.2 mL, 32 mmol) in dry 1,2-dichloroethane (50 mL) was refluxed for 20 minutes under nitrogen. The cooled reaction mixture was concentrated in vacuo, and the residue was dissolved in water (100 mL) and washed with diethyl ether (3×75 mL). The water was removed in vacuo, and the resulting solid was recrystallized from water and isopropanol to afford [2-(8,9-dioxo-2,6-diazabicyclo[5.2.0]non-1(7)-en-2yl)ethyl]phosphonic acid one fifth hydrate as a yellow solid (0.91 g, 78%, mp 260°-278° C. dec); IR (K Br, cm$^{-1}$): 1800; $^1$H NMR (DMSO 1 drop of DCl, 400 MHz): δ 3.85-3.79 (m, 2H), 3.35-3.32 (m, 2H), 3.25-3.23 (m, 2H), 1.97-1.87 (m, 4H).

Elemental analysis for C$_9$H$_{13}$N$_2$O$_5$P.1/5H$_2$O: Calc'd: C, 40.98; H, 5.12; N, 10.68. Found: C, 40.98; H, 4.98; N, 10.38.

EXAMPLE 9

[2-(4-Hydroxy-8,9-dioxo-2,6-diazabicyclo[5,2,0]non-1(7)en-2-yl)ethyl]phosphonic acid A solution of 1,3-diamino-2-hydroxypropane (27.0 g, 0.300 mol) in dry acetonitrile (270 mL) was maintained at ambient temperature with a water bath and was treated with di-t-butyl dicarbonate (23.0 mL, 0.100 mol) in acetonitrile (90 mL) over 2 hours with vigorous mechanical stirring and then was left overnight. The reaction mixture was concentrated in vacuo and the residue was dissolved in brine (250 mL) to which bromocresol green was added. The mixture was treated with 1N hydrochloric acid solution until it just turned yellow, washed with dichloromethane (3×250 mL), and then made basic (pH 12) by the addition of 2.5N sodium hydroxide solution. The product was extracted into chloroform (15×250 mL), dried with sodium sulfate, and concentrated to yield (3-amino-2-hydroxypropyl)-carbamic acid 1,1-dimethylethyl ester as a white solid (7.76 g, 41%, mp 77°-79° C.); IR (KBr, cm$^{-1}$): 3360, 1680; MS (+FAB): 191 (MH$^+$, 42), 135 (100), 58 (78); $^1$H NMR (CDCl$_3$, 400 MHz): δ5.04 (br s, NH), 3.65-3.60 (m, 1H), 3.34-3.22 (m, 1H), 3.12-3.05 (m, 1H), 2.83 (d of d, J=13 and 4 Hz, 1H), 2.63 (d of d, J=13 and 7.5 Hz, 1H), 1.44 (s, 9H).

A solution of (3-amino-2-hydroxypropyl)carbamic acid 1,1-dimethylethyl ester (7.73 g, 41 mmol), sodium carbonate (6.52 g, 62 mmol) and diethyl 2-bromoethylphosphonate (11.8 mL, 65 mmol) in absolute ethanol (150 mL) was prepared under nitrogen. This mixture was refluxed overnight and was then concentrated in vacuo. The residue was dissolved in chloroform (150 mL) and then preadsorbed onto silica gel and purified by flash chromatography (7 cm diameter, gradient elution with 2.5-20% methanol in dichloromethane) to yield [3-[[2-(diethoxyphosphinyl)ethyl]amino]-2-hydroxypropyl]carbamic acid 1,1-dimethylethyl ester as a colorless oil (11.16 g, 77%); IR (neat, cm$^{-1}$): 3320, 1710, 1250, 1170, 1040; MS (+FAB): 355 (MH$^+$, 68), 255 (90), 58 (100); $^1$H NMR (CDCl$_3$, 400 MHz): δ 5.23 (br s, NH), 4.16-4.05 (m, 4H), 3.77 (m, 1H), 3.32-2.90 (m, 4H), 2.73 (d of d, J=12 and 3.5 Hz, 1H), 2.58 (d of d, J=12 and 8.5 Hz, 1H), 2.00 (d of t, J=18 and 7 Hz, 2H), 1.43 (s, 9H), 1.32 (t, J=7 Hz, 6H).

To a solution of 3,4-diethoxy-3-cyclobutene-1,2-dione (5.0 mL, 34 mmol) in absolute ethanol (180 mL) prepared under nitrogen, was added a solution of [3-[[2-(diethoxyphosphinyl)ethyl]amino]-2-hydroxypropyl]-carbamic acid 1,1-dimethylethyl ester (12.11 g, 34 mmol) in ethanol (60 mL) over 1 hour. The reaction mixture was stirred at room temperature overnight and then concentrated in vacuo. The residue was dissolved in chloroform (150 mL), preadsorbed onto silica gel, and purified by flash chromatography (7 cm diameter, gradient elution with 2.5-15% methanol in dichloromethane) to yield [3-[[2-(diethoxyphosphinyl)ethyl](2-ethoxy-3,4-dioxo-1-cyclobuten-1-yl)amino]-2-hydroxypropyl]carbamic acid 1,1-dimethylethyl ester as a clear viscous oil (11.34 g, 70%); IR (neat, cm$^{-1}$): 3350, 1800, 1700: $^1$H NMR (CDCl$_3$, 400 MHz): δ 5.37, 5.19 (br s, NH), 4.82-4.72 (m, 3H), 4.16-3.11 (m, 11H), 2.24-2.14 (m, 2H), 1.47-1.43 (m, 12H), 1.32 (t, J=7 Hz, 6H).

A solution of [3-[[2-(diethoxyphosphinyl)ethyl](2-ethoxy-3,4-dioxo-1-cyclobuten-1-yl)amino]-2-hydroxypropyl]carbamic acid 1,1-dimethylethyl ester (11.34 g, 24 mmol) in 96% formic acid (100 mL) was prepared under nitrogen and stirred at room temperature overnight. The reaction mixture was then concentrated in vacuo to yield a thick yellow oil, which was dissolved in absolute ethanol (120 mL) and added dropwise over 1.5 hours to a solution of diisopropylethylamine (16.7 mL, 96 mmol) in absolute ethanol (360 mL). After refluxing overnight the reaction mixture was concentrated in vacuo and the residue was dissolved in chloroform (150 mL), preadsorbed onto silica gel and purified by flash chromatogrtaphy (9 cm diameter, gradient elution with 5–20% methanol in dichloromethane) to yield [2-(4-hydroxy-8,9-dioxo-2,6-diazabicyclo[5.2.0]-non-1(7)-en-2-yl)ethyl]phosphonic acid diethyl ester as a white solid (5.94 g, 74%, mp 169°–171° C.); IR (KBr, $cm^{-1}$): 3330, 3200, 1800, 1250, 1030; MS (+FAB): 333 ($MH^+$, 100), 185 (50), 179 (78); $^1H$ NMR ($CDCl_3$, 400 MHz): δ 7.18 (br s, NH), 4.52–4.44 (m, 1H), 4.20 (m, 1H), 4.14–4.04 (m, 4H), 3.79–3.70 (m, 2H), 3.57–3.54 (m, 2H), 3.36 (d, J=14 Hz, 1H), 2.33–2.13 (m, 2H), 1.32 (d of t, J=13 and 7 Hz, 6H).

Elemental analysis for $C_{13}H_{21}N_2O_6P$: Calc'd: C, 46.89; H, 6.37; N, 8.43. Found: C, 47.07; H, 6.11; N, 8.37.

To a solution of [2-(4-hydroxy-8,9-dioxo-2,6-diazabicyclo[5.2.0]non-1(7)-en-2-yl)ethyl]phosphonic acid diethyl ester (2.5 g, 7.5 mmol) in dry 1,2-dichloroethane (100 mL) under nitrogen, was added bromotrimethylsilane (9.2 mL, 60 mmol). The reaction mixture was refluxed for 20 min and then concentrated in vacuo to yield a yellow-orange foam, which was dissolved in water (100 mL). The water was washed with ether (3×100 mL) and then concentrated in vacuo to yield a solid which was recrystallized from water in isopropanol to yield [2-(4-hydroxy-8,9-dioxo-2,6-diazabicyclo[5.2.0]non-1(7)-en-2-yl)ethyl]phosphonic acid one sixth hydrate as a pale yellow solid (1.79 g, 86%, mp 268°–270° C. dec); IR (KBr, $cm^{-1}$): 3480, 3220, 1820; MS (−FAB): 275 (M-H, 22), 148 (100); $^1H$ NMR (DMSO 1 drop of DCl, 400 MHz): δ 3.90 (m, 1H), 3.85–3.74 (m, 2H), 3.46 (d, J=13 Hz, 1H), 3.34 (d of d, J=13 and 7 Hz, 1H), 3.28 (m, 2H), 1.98–1.89 (m, 2H).

Elemental analysis for $C_9H_{13}N_2O_6P \cdot 1/6\ H_2O$: Calc'd: C, 38.72; H, 4.81; N, 10.03. Found: C, 38.46; H, 4.59; N, 10.03.

a) Following the procedure of Example 9, with the exception that 2,2-dimethyl-1,3-propanediamine was employed as the reactant, gives [2-(4,4-dimethyl-8,9-dioxo-2,6-diazabicyclo[5.2.0]non-1(7)-en-2-yl)ethyl]-phosphonic acid mono hydrate, mp 265°–282° C. (dec).

Elemental analysis for $C_{11}H_{17}N_2O_5P \cdot H_2O$ Calc'd: C, 43.14; H, 6.25; N, 9.15. Found: C, 42.98; H, 6.04; N, 9.02.

b) Following the procedure of Example 9, with the exception that 1,3-propanediamine and diethyl 3-bromopropylphosphonate are the reactants, gives [3-(8,9-dioxo-2,6-diazabicyclo[5.2.0]non-1(7)-en-2-yl)propyl]phosphonic acid, mp 244°–248° C.

Elemental analysis for $C_{10}H_{15}N_2O_5P$: Calc'd: C, 43.80; H, 5.51; N, 10.23. Found: C, 43.93; H, 5.42; N, 10.18.

c) Following the procedure of Example 9, with the exception that 1,3-propanediamine and diethyl (E)-(3-chloro-1-propenyl)phosphonate are the reactants, gives [(E)-3-(8,9-dioxo-2,6-diazabicyclo[5.2.0]non-1(7)-en-2-yl)-1-propenyl]phosphonic acid one sixth hydrate, mp 255°–275° C. (dec).

Elemental analysis for $C_{10}H_{13}N_2O_5P \cdot 1/6\ H_2O$: Calc'd: C, 43.64; H, 4.88; N, 10.18. Found: C, 43.69; H, 4.68; N, 10.02.

EXAMPLE 10

8,9-Dioxo-2,6-diazabicyclo[5.2.0]non-1(7)-ene-2-acetic acid

A solution of (3-aminopropyl)carbamic acid phenylmethyl ester (7.08 g, 34 mmol) and N,N-diisopropylethylamine (4.5 mL, 26 mmol) in anhydrous dimethylformamide (100 mL) under nitrogen was cooled to 10° C. and treated with t-butyl bromoacetate (2.80 mL, 17 mmol) over 5 minutes. After one hour the bath was removed and the reaction mixture was stirred overnight, poured into water (500 mL), and made basic (pH 12) with 2.5N sodium hydroxide solution. The aqueous layer was extracted with dichloromethane (2×250 mL), which was dried over sodium sulfate and concentrated in vacuo with heat to remove dimethylformamide. The residue was purified by flash chromatography (9 cm diameter, gradient elution with 2.5–3.5% methanol in dichloromethane) to yield [3-[[(1,1-dimethylethyloxycarbonyl)methyl]amino]propyl]carbamic acid phenylmethyl ester as a pale yellow oil (4.50 g, 82%); $^1H$ NMR ($CDCl_3$, 200 MHz): δ 7.35 (m, 5H), 5.43 (br s, NH), 5.09 (s, 2H), 3.35–3.24 (m, 4H), 2.68 (t, J=6.5 Hz, 2H), 1.68 (p, J=6.5 Hz, 2H), 1.46 (s, 9H).

An ethanolic solution (60 mL) of [3-[[(1,1-dimethylethyloxycarbonyl)methyl]amino]propyl]carbamic acid phenylmethyl ester (4.49 g, 13.9 mmol) under nitrogen was added to 3,4-diethoxy-3-cyclobutene-1,2-dione (2.0 mL, 13 mmol) in the same solvent (60 mL) over 1 hour. After 3.5 more hours, the reaction mixture was preadsorbed onto silica gel and purified by flash chromatography (7.5 cm diameter, gradient elution with 30 to 60% ethyl acetate in petroleum ether) to afford [3-[[(1,1-dimethylethyloxycarbonyl)methyl]-(2-ethoxy-3,4-dioxo-1-cyclobuten-1-yl)amino]propyl]carbamic acid phenylmethyl ester as a viscous colorless oil (5.26 g, 91%); MS (+CI): 447 ($MH^+$, 100), 391 (38); $^1H$ NMR ($CDCl_3$, 400 MHz): δ 7.35 (m, 5H), 5.55, 4.97 (br m, NH), 5.10 (s, 2H), 4.75, 4.73 (q, J=7 Hz, 2H), 4.29, 3.99 (s, 2H), 3.74, 3.49 (t, J=6.5 Hz, 2H), 3.29–3.22 (m, 2H), 1.84–1.75 (m, 2H), 1.48, 1.47 (s, 9H), 1.45–1.40 (m, 3H).

To a cooled (20° C.) flask containing 10% palladium on carbon (5.25 g) under nitrogen was added [3-[[(1,1-dimethylethyloxycarbonyl)methyl]-(2-ethoxy-3,4-dioxo-1-cyclobuten-1-yl)amino]propyl]carbamic acid phenylmethyl ester (5.25 g, 11.8 mmol) in ethanol (500 mL), followed by 1,4-cyclohexadiene (11 mL, 0.12 mol) over 5 min. After 5 hours, the suspension was filtered through Celite ® with generous ethanol washing (1 L). The ethanol was evaporated and the residue was dissolved in dichloromethane and purified by flash chromatography (7.5 cm diameter, gradient elution with 2.5–3% methanol in dichloromethane) to yield (8,9-dioxo-2,6-diazabicyclo[5.2.0]non-1(7)-en-2-yl)acetic acid 1,1-dimethylethyl ester as a white solid (2.59 g, 82%, mp 167°–168° C.); IR (KBr, $cm^{-1}$): 3200, 1800, 1720; MS (EI): 266 ($M^+$, 42), 210 (33), 166 (37), 165 (100), 154 (58), 138 (37), 70 (58); $^1H$ NMR (DMSO, 400 MHz): δ 8.62 (br s, NH), 4.38 (s, 2H), 3.36–3.27 (m, 4H), 1.91 (m, 2H), 1.40 (s, 9H).

Elemental analysis for $C_{13}H_{18}N_2O_4$: Calc'd: C, 58.63; H, 6.81; N, 10.52. Found: C, 58.57; H, 6.78; N, 10.40.

An ethanolic (86 mL) solution of (8,9-dioxo-2,6-diazabicyclo[5.2.0]non-1(7)-en-2-yl)acetic acid 1,1- dimethylethyl ester (2.29 g, 8.60 mmol) was treated at room temperature with 2.5N sodium hydroxide solution (3.5 mL, 8.7 mmol) and left stirring overnight. The suspension was filtered, washing with ethyl acetate to give a solid which was recrystallized from methanol/water/isopropanol (final volume 50 mL) to afford (8,9-dioxo-2,6-diazabicyclo[5.2.0]non-1(7)-en-2-yl)acetic acid sodium salt hydrate (1.43 g, 66%, mp 280°-300° C. dec); MS (-FAB): 231 (M-H, 37), 209 (M-Na, 100); $^1$H NMR (DMSO 1 drop of DCl, 400 MHz): δ 4.40 (s, 2H), 3.36-3.25 (m, 4H), 1.89 (m, 2H).

Elemental analysis for $C_9H_9N_2NaO_4 \cdot H_2O$: Calc'd: C, 43.21; H, 4.43; N, 11.20. Found: C, 43.29; H, 4.38; N, 11.32.

a) Following the procedure of Example 10, with the exception that ethyl 3-bromopropionate was employed as a reactant, gives 3-(8,9-dioxo-2,6-diazabicyclo[5.2.0]non-1(7)-en-2-yl)propanoic acid sodium salt sesquihydrate, mp 310 (dec).

Elemental analysis for $C_{10}H_{11}N_2NaO_4 \cdot 1.5\ H_2O$: Calc'd: C, 44.04; H, 4.99; N, 10.27. Found: C, 44.28; H, 5.15; N, 10.24.

EXAMPLE 11

2-[(1H-Tetrazol-5-yl)methyl]-2,6-diazabicyclo[5.2.0]-non-1(7)-ene-8,9-dione

A solution of (3-aminopropyl)carbamic acid 1,1-dimethylethyl ester (6.00 g, 34 mmol), prepared by the method of Saari et al., *J. Med. Chem.*, 33, 97 (1990), in absolute ethanol (90 mL) was treated with sodium carbonate (3.96 g, 37 mmol) followed by a solution of bromoacetonitrile (2.6 mL, 37 mmol) in ethanol (30 mL) over 45 min. After stirring at room temperature overnight, the contents of the flask were filtered, preadsorbed onto silica gel, and purified by flash chromatography (7 cm diameter, elution with 2.5% methanol in dichloromethane) to afford [3-(cyanomethylamino)-propyl]carbamic acid 1,1-dimethylethyl ester as a yellow oil (3.99 g, 55%); IR (neat, cm$^{-1}$): 3330, 2240, 1700; MS (+CI): 214 (MH+, 20), 187 (76), 158 (100), 131 (44); $^1$H NMR (CDCl$_3$, 400 MHz): δ 4.80 (br s, NH), 3.61 (s, 2H), 3.22 (q, J=6.5 Hz, 2H), 2.79 (t, J=6.5 Hz, 2H), 1.69 (p, J=6.5 Hz, 2H), 1.45 (s, 9H).

A solution of 3,4-diethoxy-3-cyclobutene-1,2-dione (2.6 mL, 18 mmol) in absolute ethanol (90 mL) was treated with [3-(cyanomethylamino)propyl]carbamic acid 1,1-dimethylethyl ester (3.90 g, 18 mmol) in ethanol (30 mL) over 90 min. After 40 hours the reaction mixture was evaporated, dissolved in dichloromethane, preadsorbed onto silica gel, and purified by flash chromatography (7 cm diameter, gradient elution with 0-5% methanol in dichloromethane) to yield [3-[(cyanomethyl)-(2-ethoxy-3,4-dioxo-1-cyclobuten-1-yl)amino]propyl]carbamic acid 1,1-dimethylethyl ester as a yellow oil (5.48 g, 90%); IR (neat, cm$^{-1}$): 3360, 1800; MS (+FAB): 282 (76), 238 (98), 158 (100); $^1$H NMR (CDCl$_3$, 400 MHz): δ 4.81 (q, J=7 Hz, 2H), 4.75 (br s, NH), 4.45, 3.66 (s, 4H), 3.84, 3.60 (br m, 2H), 3.26-3.15 (m, 2H), 1.91 (p, J=6.5 Hz, 2H), 1.50 (t, J=7 Hz, 3H), 1.45 (s, 9H).

A solution of [3-[(cyanomethyl)-(2-ethoxy-3,4-dioxo-1-cyclobuten-1-yl)amino]propyl]carbamic acid 1,1-dimethylethyl ester (5.48 g, 16 mmol) in 96% formic acid (40 mL) under nitrogen was prepared. After 24 hours the solvent was removed and the residue was dissolved in isopropanol and concentrated several times. Ethanol (40 mL) was added and the suspension was stirred overnight and filtered to afford (8,9-dioxo-2,6-diazabicyclo[5.2.0]non-1(7)-en-2-yl)acetonitrile one eighth hydrate as a white solid (1.50 g, 48%, mp 215°-218° C.); IR (KBr, cm$^{-1}$): 3220, 1810; MS (DEI): 191 (M+, 57), 135 (41), 70 (41), 43 (70), 41 (100); $^1$H NMR (DMSO, 400 MHz): δ 8.83 (br s, NH), 4.84 (s, 2H), 3.40-3.30 (m, 4H), 1.95 (m, 2H).

Elemental analysis for $C_9H_9N_3O_2 \cdot \frac{1}{8} H_2O$: Calc'd: C, 55.93; H, 4.69; N, 21.74. Found: C, 55.99; H, 4.76; N, 21.90.

To a solution of (8,9-dioxo-2,6-diazabicyclo[5.2.0]-non-1(7)-en-2-yl)acetonitrile one eighth hydrate (1.54 g, 8.0 mmol) in dry dimethylformamide (35 mL) under nitrogen, was added sodium azide (0.79 g, 12 mmol) and ammonium chloride (0.65 g, 12 mmol). The reaction mixture was slowly heated to 125° C., maintained at this temperature for 2 hours, cooled to room temperature, and then filtered. The concentrated filtrate was dissolved in water and evaporated. The residue was recrystallized from methanol to yield 2-[(1H-tetrazol-5-yl)methyl]-2,6-diazabicyclo[5.2.0]non-1(7)-ene-8,9-dione one third hydrate as off-white crystals (1.18 g, 61%, mp 264°-267° C.); IR (KBr, cm$^{-1}$): 3200, 1810; $^1$H NMR (DMSO, 400 MHz): δ 8.70 (s, NH), 5.24 (s, 2H), 3.34-3.28 (m, 4H), 1.92 (m, 2H).

Elemental analysis for $C_9H_{10}N_6O_2 \cdot \frac{1}{3} H_2O$: Calc'd: C, 45.00; H, 4.48; N, 34.98. Found: C, 45.28; H, 4.21; N, 34.76.

a) Following the procedure of Example 11, with the exception that 3-bromopropionitrile was employed as a reactant, gives 2-[2-(1H-tetrazol-5-yl)ethyl]-2,6-diazabicyclo[5.2.0]non-1(7)-ene-8,9-dione, mp 255-262 (dec).

Elemental analysis for $C_{10}H_{12}N_6O_2$: Calc'd: C, 48.38; H, 4.87; N, 33.85. Found: C, 48.10; H, 4.80; N, 34.19.

EXAMPLE 12

[2-(9,10-Dioxo-2,7-diazabicyclo[6.2.0]dec-1(8)-en-2-yl)ethyl]phosphonic acid

A solution of 1,4-diaminobutane (30 mL, 0.30 mol) in dry tetrahydrofuran (90 mL) was maintained at 0° C. and was treated with di-t-butyl dicarbonate (23 mL, 0.10 mol) in tetrahydrofuran (90 mL) over 1.5 hours with vigorous mechanical stirring and then was left overnight. The reaction mixture was concentrated in vacuo and the residue was dissolved in water (100 mL) to which bromocresol green was added. The mixture was treated with 1N hydrochloric acid solution until it just turned yellow, washed with dichloromethane (2×250 mL), and then made basic (pH 12) by the addition of 2.5N sodium hydroxide solution. The product was extracted into chloroform (6×250 mL), dried with sodium sulfate, and concentrated to yield (4-aminobutyl)carbamic acid 1,1-dimethylethyl ester as a yellow oil (13.4 g, 71%); IR (neat, cm$^{-1}$): 3350, 1700; MS (EI): 188 (M+, 4), 132 (56), 115 (33), 70 (100); $^1$H NMR (CDCl$_3$, 400 MHz): δ 4.76 (br s, NH), 3.11 (q, J=6 Hz, 2H), 2.70 (t, J=6 Hz, 2H), 1.58-1.45 (m, 4H), 1.43 (s, 9H).

A solution of (4-aminobutyl)carbamic acid 1,1-dimethylethyl ester (13.3 g, 71 mmol), sodium carbonate (11.25 g, 106 mmol) and diethyl 2-bromo-ethylphosphonate (20 mL, 104 mmol) in absolute ethanol (150 mL) was prepared under nitrogen. This mixture was refluxed overnight and was then concentrated in vacuo. The residue was dissolved in chloroform (150 mL) and then preadsorbed onto silica gel and purified by flash chromatography (7 cm diameter, gradient elution with 5-30% methanol in dichloromethane) to yield [4-[[2-(diethoxyphosphinyl)ethyl]amino]butyl]carbamic acid 1,1-dimethylethyl ester as a colorless oil (13.7 g, 55%); MS (+FAB): 353 (MH+, 100), 150 (68), 56 (83); $^1$H NMR (CDCl$_3$, 400 MHz): δ 5.01 (br s, NH), 4.17–4.03 (m, 4H), 3.15–3.08 (m, 2H), 2.92 (d of t, J=15 and 7.5 Hz, 2H), 2.84 (br s, NH), 2.66 (br t, J=7 Hz, 2H), 2.02 (d of t, J=18 and 7.5 Hz, 2H), 1.56–1.52 (m, 4H), 1.43 (s, 9H), 1.33 (t, J=7 Hz, 6H).

To a solution of 3,4-diethoxy-3-cyclobutene-1,2-dione (5.8 mL, 39 mmol) in absolute ethanol (200 mL) prepared under nitrogen, was added a solution of [4-[[2-(diethoxyphosphinyl)ethyl]amino]butyl]carbamic acid 1,1-dimethylethyl ester (13.7 g, 39 mmol) in ethanol (75 mL) over 1.75 hour. The reaction mixture was stirred at room temperature overnight and then concentrated in vacuo. The residue was dissolved in chloroform (150 mL), preadsorbed onto silica gel, and purified by flash chromatography (9 cm diameter, elution with 2.5% methanol in dichloromethane) to yield [4-[[2-(diethoxyphosphinyl)ethyl](2-ethoxy-3,4-dioxo-1-cyclobuten-1-yl)amino]butyl]carbamic acid 1,1-dimethylethyl ester as a yellow viscous oil (16.8 g, 90%).

A solution of [4-[[2-(diethoxyphosphinyl)ethyl](2-ethoxy-3,4-dioxo-1-cyclobuten-1-yl)amino]butyl]carbamic acid 1,1-dimethylethyl ester (16.8 g, 35 mmol) in 96% formic acid (100 mL) was prepared under nitrogen and stirred at room temperature overnight. The reaction mixture was then concentrated in vacuo to yield a thick yellow oil, which was dissolved in absolute ethanol (125 mL) and added dropwise over 1.5 hours to a solution of diisopropylethylamine (17 mL, 98 mmol) in absolute ethanol (375 mL). After refluxing overnight the reaction mixture was concentrated in vacuo and the residue was dissolved in chloroform (150 mL), preadsorbed onto silica gel, and purified by flash chromatography (9 cm diameter, gradient elution with 5–10% methanol in dichloromethane) to yield [2-(9,10-Dioxo-2,7-diazabicyclo[6.2.0]dec-1(8)-en-2-yl)ethyl]phosphonic acid diethyl ester as a pale yellow solid (9.65 g, 83%, mp 103°–105° C.); IR (KBr, cm$^{-1}$): 3440, 3230, 1795; MS (+FAB): 331 (MH+, 100), 109 (31); $^1$H NMR (CDCl$_3$, 400 MHz): δ 7.14 (br s, NH), 4.16–4.05 (m, 6H), 3.39–3.36 (m, 4H), 2.17 (d of t, J=19 and 7.5 Hz, 2H), 1.74–1.68 (m, 4H), 1.33 (t, J=7 Hz, 6H).

Elemental analysis for C$_{14}$H$_{23}$N$_2$O$_5$P: Calc'd: C, 50.91; H, 7.02; N, 8.48. Found: C, 50.76; H, 6.82; N, 8.37.

To a solution of [2-(9,10-Dioxo-2,7-diazabicyclo[6.2.0]dec-1(8)-en-2-yl)ethyl]phosphonic acid diethyl ester (7.60 g, 23 mmol) in dry 1,2-dichloroethane (300 mL) under nitrogen, was added bromotrimethylsilane (25 g, 160 mmol). The reaction mixture was refluxed for 25 min and then concentrated in vacuo to yield a dark rust oil, which was dissolved in water (250 mL). The water was washed with ether (3×250 mL) and then concentrated in vacuo to yield a yellow orange solid which was recrystallized from water (100 mL) to yield [2-(9,10-Dioxo-2,7-diazabicyclo[6.2.0]dec-1(8)-en-2-yl)ethyl]phosphonic acid hydrate as a tan solid (3.80 g, 60%, mp 266°–271° C. dec); IR (KRr, cm$^{-1}$): 3350, 3260, 1800; MS (−FAB): 273 (M-H); $^1$H NMR (DMSO, 400 MHz): δ 8.32 (br s, NH), 3.94–3.87 (m, 2H), 3.31–3.28 (m, 2H), 3.22–3.18 (m, 2H), 1.96–1.87 (m, 2H), 1.61–1.49 (m, 4H).

Elemental analysis for C$_{10}$H$_{15}$N$_2$O$_5$P·H$_2$O: Calc'd: C, 41.10; H, 5.86; N, 9.59. Found: C, 41.22; H, 5.76; N, 9.65.

In a manner analogous to the procedures of Examples 7 and 8, the following compounds are obtained:

| Example | Compound |
|---------|----------|
| 13 | [(E)-3-(7,8-Dioxo-2,5-diazabicylco[4.2.0]oct-1(6)-en-2-yl)-1-propenyl]phosphonic acid |
| 14 | [3-(7,8-Dioxo-2,5-diazabicyclo[4.2.0]oct-1(6)-en-2-yl)propyl]phosphonic acid |

It was determined that the compounds of this invention are competitive NMDA antagonists by determining their ability to inhibit binding of 3-(2-carboxypiperazinyl-4-yl)propyl-1-phosphonic acid (CPP), a known competitive NMDA antagonist, at NMDA receptors in rat brain homogenate. In a manner similar to the procedure of Murphy et al., J. Pharmacol. Exp. Therap. 240 (3) 778 (1987), rat brain homogenates from which endogenous glutamate had been removed were incubated with (3H)CPP (8 nM), the compound being tested and then buffer each for 15 minutes at 23° C. to obtain a final volume of 2 milliliters. The amount of radio ligand displaced by the test compound is expressed as a percentile of the radio ligand displaced by NMDA. The inhibitory concentration of test compound that will displace 50% of the labeled CPP is determined from dose-response evaluations.

The properties of these compounds were also directly established by demonstrating the NMDA antagonist properties of representative compounds in male Swiss-albino mice (CD-1 strain, Charles River) 18–22 grams in weight after 18 hours of food deprivation which had been habituated to an observation chamber for 30 minutes. The mice were pretreated with the representative test compounds followed thirty minutes later with NMDA (195 mg/kg, i.p., the ED$_{90}$ dose for generalized myoclonus). The mice were then observed for 30 minutes, noting the latency of onset of generalized myoclonus (uncontrollable hind leg scratching of limbs and/or torso muscle jerking with loss of righting reflex) and death. From the latter, the ED$_{50}$ for survival is determined. In this standard experimental test procedure, the specific compounds tested and their activity, which representatively establish the activity for all the compounds herein, is presented in the following Table.

TABLE

| Compound of Example | CPP Binding IC$_{50}$ (μM) | NMDA Induced Lethality ED$_{50}$ (mg/kg) |
|---------|---------|---------|
| 1 | 1.6 | >100 |
| 1(a) | 190 | >100 |
| 1(b) | 2.3 | >100 |
| 1(c) | 10.2 | >100 |
| 2 | 5.2 | >100 |
| 2(a) | 19.6 | >100 |
| 2(b) | >100 | >100 |
| 3 | 10.5 | >100 |
| 3(a) | 30 | >100 |
| 3(b) | 50% (100) | >100 |
| 4 | 0.471 | 28.7 |
| 4(a) | >10 | >100 |
| 4(b) | 2.59 | >100 |
| 4(c) | 68% (10) | >30 |
| 5 | 52% (10) | >30 |
| 6 | 1.0 | 50% (50) |
| 6(a) | >10 | >150 |
| 7 | 0.092 | 6.2 |
| 8 | 0.030 | 2.1 |
| 9 | 0.019 | 1.8 |
| 9(a) | 0.28 | 50% (5) |
| 9(b) | >1 | >10 |
| 9(c) | >10 | >5 |
| 10 | 0.55 | >20 |
| 10(a) | 0.34 | >20 |
| 11 | 0.038 | >10 |

TABLE-continued

| Compound of Example | CPP Binding IC$_{50}$ ($\mu$M) | NMDA Induced Lethality ED$_{50}$ (mg/kg) |
|---|---|---|
| 11(a) | 40% (10) | >5 |
| 12 | 0.041 | 80% (5) |

Where the displacement of CPP binding is expressed as a percentage, it is at the $\mu$M concentration given at the concentration in the parenthesis. Similarly, where percent inhibition of lethality at dose in parenthesis.

Thus, the compounds of this invention demonstrate the ability to antagonize NMDA-induced lethality in vivo in mice. They compete with 3-(2-carboxypiperazinyl-4-yl)-propyl-1-phosphonic acid (CPP), a known competitive NMDA-antagonist, for its binding site. The compounds of the present invention are, therefore, competitive NMDA antagonists.

The compounds of the present invention are active against NMDA-induced lethality and are useful in the treatment of CNS disorders such as convulsions, brain cell damage and related neurodegenerative disorders, including senile dementia, Alzheimer's disease, Huntingdon's chorea, stroke, hypoglycemia, cerebral palsy, cerebral ischemia, epilepsy, and olivo-ponto cerebellar atrophy.

Hence, there is herewith provided in addition to the novel compounds, supra, a method for preventing neurodengenerative disorders induced by overstimulation of NMDA receptors in brain and spinal cord by excitatory amino acids, which comprises administering to a mammal suffering from such degenerative disease states, an anticonvulsant, neuroprotective amount of an NMDA antagonist of this invention.

As such, the compounds of this invention may be administered neat or with a pharmaceutical carrier to a patient in need thereof. The pharmaceutical carrier may be solid or liquid.

Accordingly, this invention also provides a pharmaceutical composition comprising a compound of formula I as shown and defined hereinabove or a pharmaceutically acceptable salt thereof and a pharmaceutically acceptable carrier.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

To determine the effective amount of compound to be administered in alleviation of CNS degenerative dysfunctions, the physician need only evaluate the effects of a given NMDA antagonist in the patient by incrementally increasing the oral dosage from about 1 mg/kg to about 20 mg/kg until the desired symptomatic relief level is achieved. The continuing dose regimen may then be modified to achieve the desired result, with the range of about 1 to 100 mg/day. Similar techniques are followed by determining the effective dose range upon i.v. or i.m. administration. When using the compounds prophylactically to arrest declining cognitive function as in Alzheimer's dementia, a more subjective approach is taken such as by relating the drug dosage to improved memory responses or analogous desired responses which can be related to relief of overstimulation of the excitatory amino acid receptors.

What is claimed is:

1. A compound of the formula:

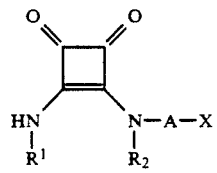

in which
R$^1$ is hydrogen, alkyl of 1 to 6 carbon atoms or phenylalkyl of 7 to 12 carbon atoms;
R$^2$ is hydrogen, alkyl of 1 to 6 carbon atoms, alkenyl of 2 to 6 carbon atoms, or phenylalkyl of 7 to 12 carbon atoms;
A is alkylene of 1 to 6 carbon atoms or alkenylene of 2 to 6 carbon atoms; and X is $CO_2R^3$ in which $R^3$ is hydrogen or alkyl of 1 to 6 carbon atoms, $P(O)(OR^4)(OR^5)$ in which $R^4$ and $R^5$ are, independently, hydrogen or alkyl of 1 to 6 carbon atoms, 3,5-dioxo-1,2,4-oxadiazolidin-2-yl or 5-tetrazolyl;

or a pharmaceutically acceptable salt thereof.

2. A compound of claim 1 in which $R^1$ and $R^2$ are, independently, hydrogen, methyl, allyl, methallyl or benzyl; A is alkylene of 1 to 4 carbon atoms or trans 2-butenylene and X is a carboxyl, phosphonyl or 5-tetrazolyl group; or a pharmaceutically acceptable salt thereof.

3. A method for preventing convulsions and neurodegenerative disorders induced by overstimulation of excitatory amino acid receptors, which comprises administering to a mammal suffering from such convulsions or neurodegenerative disorders, an anticonvulsant, neuroprotective amount of an NMDA antagonist of the formula:

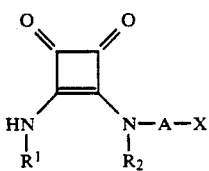

in which $R^1$ is hydrogen, alkyl of 1 to 6 carbon atoms or phenylalkyl of 7 to 12 carbon atoms;

$R^2$ is hydrogen, alkyl of 1 to 6 carbon atoms, alkenyl of 2 to 6 carbon atoms or phenylalkyl of 7 to 12 carbon atoms;

A is alkylene of 1 to 6 carbon atoms or alkenylene of 2 to 6 carbon atoms; and

X is $CO_2R^3$ in which $R^3$ is hydrogen or alkyl of 1 to 6 carbon atoms, $P(O)(OR^4)(OR^5)$ in which $R^4$ and $R^5$ are, independently, hydrogen or alkyl of 1 to 6 carbon atoms, 3,5-dioxo-1,2,4-oxadiazolidin-2-yl or 5-tetrazolyl;

or a pharmaceutically acceptable salt thereof.

4. A method for preventing brain cell damage resulting from overstimulation by excessive amounts of excitatory amino acids which comprises administering to a mammal suffering from neurodegeneration an effective amount of an NMDA antagonist of the formula:

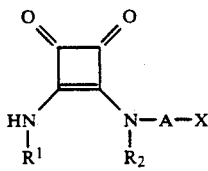

in which $R^1$ is hydrogen, alkyl of 1 to 6 carbon atoms or phenylalkyl of 7 to 12 carbon atoms;

$R^2$ is hydrogen, alkyl of 1 to 6 carbon atoms, alkenyl of 2 to 6 carbon atoms or phenylalkyl of 7 to 12 carbon atoms;

A is alkylene of 1 to 6 carbon atoms or alkenylene of 2 to 6 carbon atoms; and

X is $CO_2R^3$ in which $R^3$ is hydrogen or alkyl of 1 to 6 carbon atoms, $P(O)(OR^4)(OR^5)$ in which $R^4$ and $R^5$ are, independently, hydrogen or alkyl of 1 to 6 carbon atoms, 3,5-dioxo-1,2-oxadiazolidin-2-yl or 5-tetrazoyl;

or a pharmaceutically acceptable salt thereof.

5. The compound of claim 1 which is N-(2-amino-3,4-dioxo-1-cyclobuten-1-yl)beta-alanine, or a pharmaceutically acceptable salt thereof.

6. A compound of claim 1 which is N-(2-amino-3,4-dioxo-1-cyclobutenyl)glycine ethyl ester, N-(2-amino-3,4-dioxo-1-cyclobutenyl)glycine, 4-[(2-amino-3,4-dioxo-1-cyclobutenyl)amino]butanoic acid, or a pharmaceutically acceptable salt thereof.

7. The compound of claim 1 which is 2-[2-[(2-amino-3,4-dioxo-1-cyclobuten-1-yl)amino]ethyl]-1,2,4-oxadiazolidine-3,5-dione.

8. A compound of claim 1 which is N-[2-(methylamino)-3,4-dioxo-1-cyclobutenyl]beta-alanine, 3-[[3,4-dioxo-2[(phenylmethyl)amino]-1-cyclobutenyl]-amino]propanoic acid, or a pharmaceutically acceptable salt thereof.

9. The compound of claim 1 which is N-(2-amino-3,4-dioxo-1-cyclobuten-1-yl)-N-(2-propenyl)glycine, or a pharmaceutically acceptable salt thereof.

10. A compound of claim 1 which is N-(2-amino-3,4-dioxo-1-cyclobutenyl)-N-(2-methyl-2-propenyl)glycine, N-(2-amino-3,4-dioxo-1-cyclobutenyl)-N-(phenylmethyl)glycine, or a pharmaceutically acceptable salt thereof.

11. The compound of claim 1 which is [2-[(2-amino-3,4-dioxo-1-cyclobuten-1-yl)amino]ethyl]phosphonic acid, or a pharmaceutically acceptable salt thereof.

12. A compound of claim 1 which is [[(2-amino-3,4-dioxo-1-cyclobutenyl)amino]methyl]phosphonic acid, [3-[(2-amino-3,4-dioxo-1-cyclobuten-1-yl)amino]-propyl]phosphonic acid, [4[(2-amino-3,4-dioxo-1-cyclobuten-1-yl)amino]-butyl]phosphonic acid, or a pharmaceutically acceptable salt thereof.

13. The compound of claim 1 which is [(E)-4-[(2-amino-3,4-dioxo-1-cyclobutenyl-1-yl)amino]-2-butenyl]phosphonic acid, or a pharmaceutically acceptable salt thereof.

14. The compound of claim 1 which is [2-[(2-amino-3,4-dioxo-1-cyclobuten-1-yl)methylamino]ethyl]phosphonic acid, or a pharmaceutically acceptable salt thereof.

15. A compound of claim 1 which is [[(2-amino-3,4-dioxo-1-cyclobuten-1-yl)methylamino]methyl]phosphonic acid, or a pharmaceutically acceptable salt thereof.

* * * * *